(12) United States Patent  (10) Patent No.: US 7,420,171 B2
Hopkins et al.  (45) Date of Patent: Sep. 2, 2008

(54) GAS SENSORS

(75) Inventors: Graham Paul Hopkins, Chelmsford (GB); Andrew Stephen Hayward, Witham (GB); Brian Thomas Alfred Wells, Braintree (GB)

(73) Assignee: E2V Technologies (UK) Limited, Chelmsford (GB)

( * ) Notice: Subject to any disclaimer, the term of this patent is extended or adjusted under 35 U.S.C. 154(b) by 0 days.

(21) Appl. No.: 10/537,770

(22) PCT Filed: Dec. 5, 2003

(86) PCT No.: PCT/GB03/05333

§ 371 (c)(1),
(2), (4) Date: Oct. 25, 2005

(87) PCT Pub. No.: WO2004/051240

PCT Pub. Date: Jun. 17, 2004

(65) Prior Publication Data

US 2006/0138328 A1    Jun. 29, 2006

(30) Foreign Application Priority Data

Dec. 5, 2002 (GB) ................................ 0228398.4

(51) Int. Cl.
*G01J 5/02* (2006.01)
(52) U.S. Cl. .................................................. 250/339.13
(58) Field of Classification Search ............. 250/339.13
See application file for complete search history.

(56) References Cited

U.S. PATENT DOCUMENTS

| | | | |
|---|---|---|---|
| 3,465,147 A | 9/1969 | Banville | |
| 4,700,079 A * | 10/1987 | Ito | ............................... 250/574 |
| 4,946,092 A * | 8/1990 | van Poorten | ................. 228/162 |
| 5,060,508 A * | 10/1991 | Wong | .......................... 73/31.02 |
| 5,347,223 A * | 9/1994 | Krcma et al. | ................ 324/455 |
| 5,457,320 A | 10/1995 | Eckles et al. | |
| 5,604,587 A | 2/1997 | Che et al. | |
| 5,747,808 A * | 5/1998 | Wong | .......................... 250/343 |
| 6,046,814 A * | 4/2000 | Karlsson et al. | ............. 356/437 |

FOREIGN PATENT DOCUMENTS

| | | |
|---|---|---|
| DE | 102 16 047 | 10/2003 |
| EP | 1 229 322 | 8/2002 |
| FR | 2 767 195 | 2/1999 |
| GB | 762285 A | 11/1956 |
| GB | 2 349 207 | 10/2000 |
| JP | 6-34544 | 8/1994 |

* cited by examiner

*Primary Examiner*—David P. Porta
*Assistant Examiner*—Marcus H Taningco
(74) *Attorney, Agent, or Firm*—Venable LLP; Robert Kinberg; Kyle D. Petaja (57) ABSTRACT

A gas sensor comprises a body on which is mounted an optical source and a detector means sensitive to light from the source. The body further comprises a channel arranged to admit gas, the channel comprising an elongated groove having reflective surfaces defining a folded optical path for light from the source. The groove is arranged as a serpentine shape or spiral shape so that light from the source to detector travels around the groove being internally reflected within the shape.

16 Claims, 16 Drawing Sheets

GAS SENSORS

This invention relates to apparatus for, and methods of, sensing gasses. The invention particularly relates to such methods and devices in which optical radiation is transmitted through a gas and subsequently detected to provide information concerning the gas.

In a typical gas monitor, an infrared source is arranged to emit radiation, which passes through a gas to be monitored. Infrared radiation is absorbed by the gas and that remaining is subsequently detected by an infrared detector. A comparison is made between the source intensity and the intensity of radiation detected following passage through the gas to give the concentration of a target gas.

The present invention seeks to provide a gas monitor having improved characteristics over those previously known.

The invention provides a gas sensor comprising a body, on which is mounted an optical source and detector means sensitive to light from the source, the body further comprising a channel arranged to admit gas, the channel comprising an elongated groove having reflective surfaces defining a folded optical path for light from the source.

The invention permits a gas sensor having a folded optical path to be manufactured more simply than hitherto. Previously, folded optical paths were provided by means of tubular structures. A problem which may be encountered with such structures is the difficulty in plating or otherwise making the interior of the tubes sufficiently reflective of infrared radiation.

Advantageously, the source is located at one end portion of the channel and the detector is located at the other. This ensures that radiation emitted from the source travels a long optical path.

Preferably, a second detector is provided and arranged to detect radiation that has been tapped off partway along the channel. This feature provides detection for radiation that has travelled a shorter optical path than has radiation reaching the detector at the end of the channel. Thus, gases having different infrared absorption characteristics may be detected.

The folded optical path may be spiral, serpentine or helical.

The optical source is preferably an infrared source but sources and detectors operating in other parts of the optical spectrum may be used in other embodiments.

The invention will now be described, by way of example, with reference to the accompanying drawings, in which:

FIG. 9 is a partly sectional side view of the body of FIG. 8;

Figure 1:
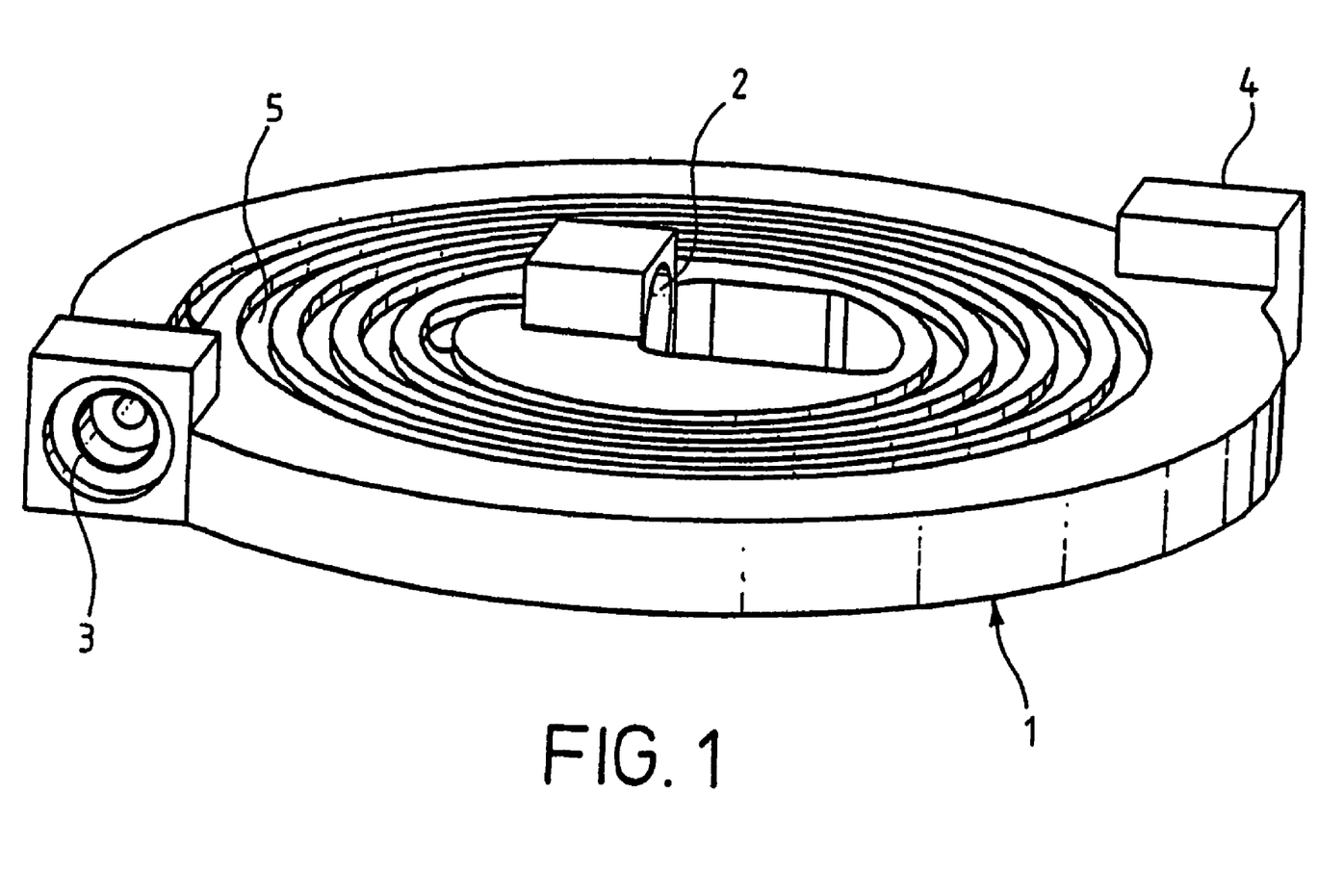
FIG. 1 is a perspective schematic view of the body of a gas sensor constructed according to a first embodiment of the invention.

With reference to FIG. 1, the body of a gas sensor constructed according to the invention is shown and indicated generally by the reference numeral 1. The body includes a cavity 2, arranged to accommodate a source of infrared light. A second cavity 3 is also provided and, in use, is arranged to accommodate a detector of light from the source. A third cavity 4 is provided to accommodate a second detector arrangement.

In accordance with the invention, the body 1 includes a channel formed by an elongated groove 5 in the body. The groove 5 forms a folded optical path for light travelling from the source to the detector. In this embodiment, the groove 5 is in the form of a spiral, with the cavity 2 for the source being located at the inner end portion of the groove 5. The cavity 3 associated with the first detector is located at the outer end portion of the spiral channel. The cavity 4 associated with the second detector is located at the periphery of the body 1, adjacent the channel. The spiral substantially occupies a flat plane.

Figure 2:
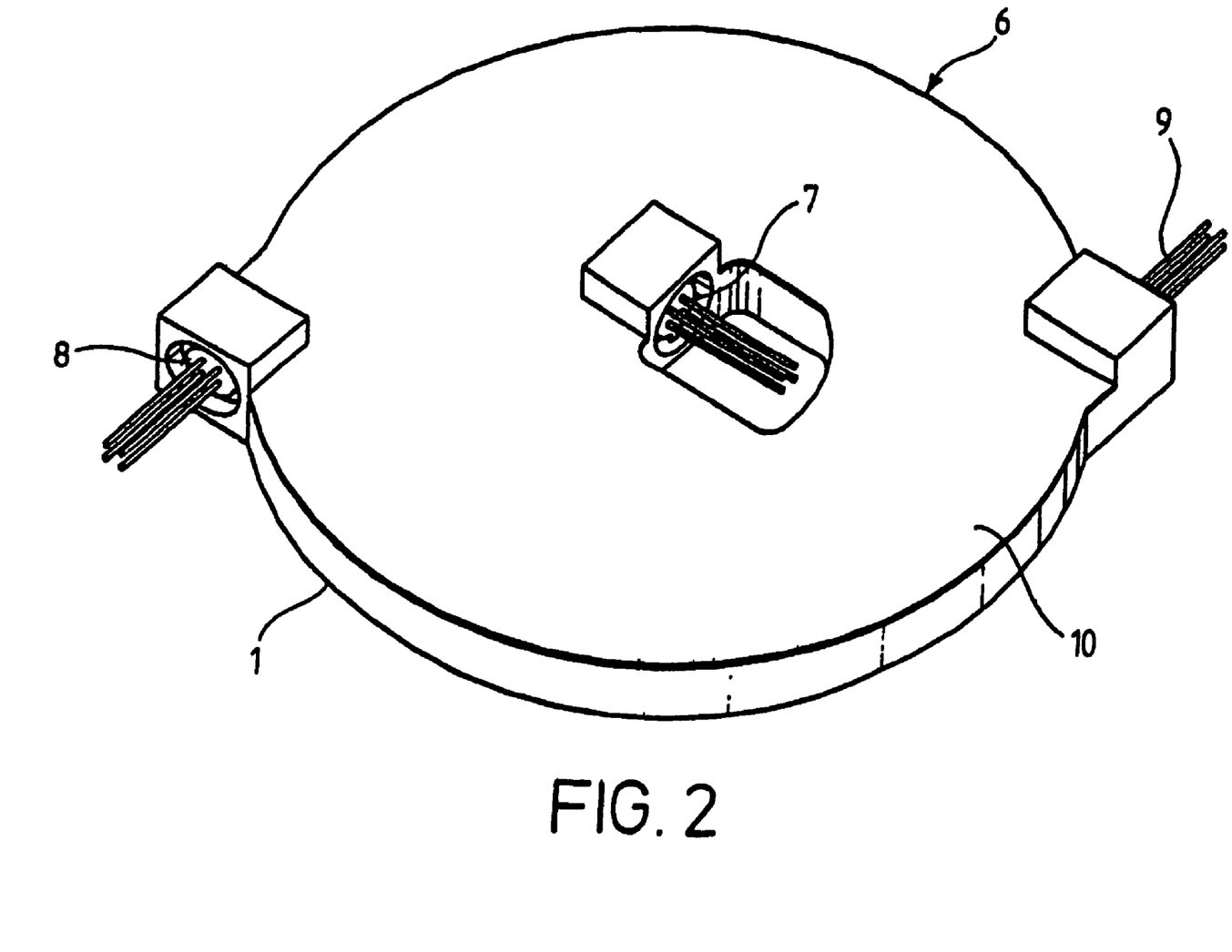
FIG. 2 is a perspective schematic view of a gas sensor constructed according to the invention incorporating the body of FIG. 1.

FIG. 2 illustrates a gas sensor 6 incorporating the body 1 of FIG. 1. The sensor comprises the body 1 and a source 7 of infrared radiation, the electrical connections of which are visible in this drawing. Light emitted by the source 7 is transmitted along the spiral path by means of successive reflections.

A first detector arrangement 8 is provided in order to detect radiation having travelled the complete spiral optical path. A second detector arrangement 9 is arranged to detect radiation having travelled a portion of the spiral optical path. Means are provided (but are not viewable in these drawings) to tap off a portion of light at a predetermined position on the optical path, which portion is directed towards the second detector arrangement 9. The remainder of the light is reflected around the spiral to the first detector arrangement 8.

The optical path length between the source 7 and the first detector 8 is relatively long, compared with the optical path length between the source and the second detector 9. Hence, the first detector 8 may be suitable for detecting gases having low IR absorption characteristics.

The gas sensor also comprises a lid 10 arranged to cover the body 1. The lid 10 includes gas admittance means, which may take the form of a sinter, mesh, goretex membrane or perforated metal sheet, for example. The gas admittance means ensures that a sample of gas is admitted into the channel. The interior surface of the lid 10 is highly reflective of infrared radiation. This may be achieved by plating the interior surfaces of the lid 10 with gold.

The components of each detector arrangement 8, 9 are not visible in these drawings but typically comprise an active detector and a reference detector. The active detector includes a bandpass filter, arranged to be transparent to the strong fundamental absorption band of the gas being detected. The reference detector is located adjacent to the active detector and is used to compensate for changes in operating conditions and with time. The reference detector includes a different filter to that fitted in the active detector and does not respond to the target gas. By comparing the signals from the active detector and the reference detector, the user can discriminate the signal reduction due to the target gas, from that due to ambient and physical variations. The reference detector is preferably located immediately adjacent the active detector so that the active detector and reference collect radiation that has travelled similar optical paths. To aid this, the reference and the active detector may be contained in a single detector package.

In use, the source 7 produces broadband IR radiation, which is reflected successively by the reflective surfaces of the spiral channel and absorbed by the gas in the housing to a degree proportional to the amount of gas present. A portion of the radiation being reflected along the groove 5 is tapped off to the detector arrangement 9. The remainder of the radiation continues to be reflected along the spiral path and is detected at the first detector arrangement 8 at the end of the channel.

A range of wavelengths of the broadband IR radiation not absorbed by the gas is detected at the respective detector arrangements 8, 9. Each detector 8, 9 generates an electrical signal corresponding to the strength of the detected IR radiation. This signal is input to processing electronics (not shown) arranged to determine the concentration of gas present in the housing. The concentration is related to the intensity by the following equation:

$$I = I_o e^{-ecl}$$

where I is the intensity of radiation detected by the detector, $I_o$ is the intensity of radiation emitted at the source, e is effectively a constant which is dependent on the particular gas being monitored, c is the gas concentration and l is the distance travelled by the radiation through the gas.

Figure 3:
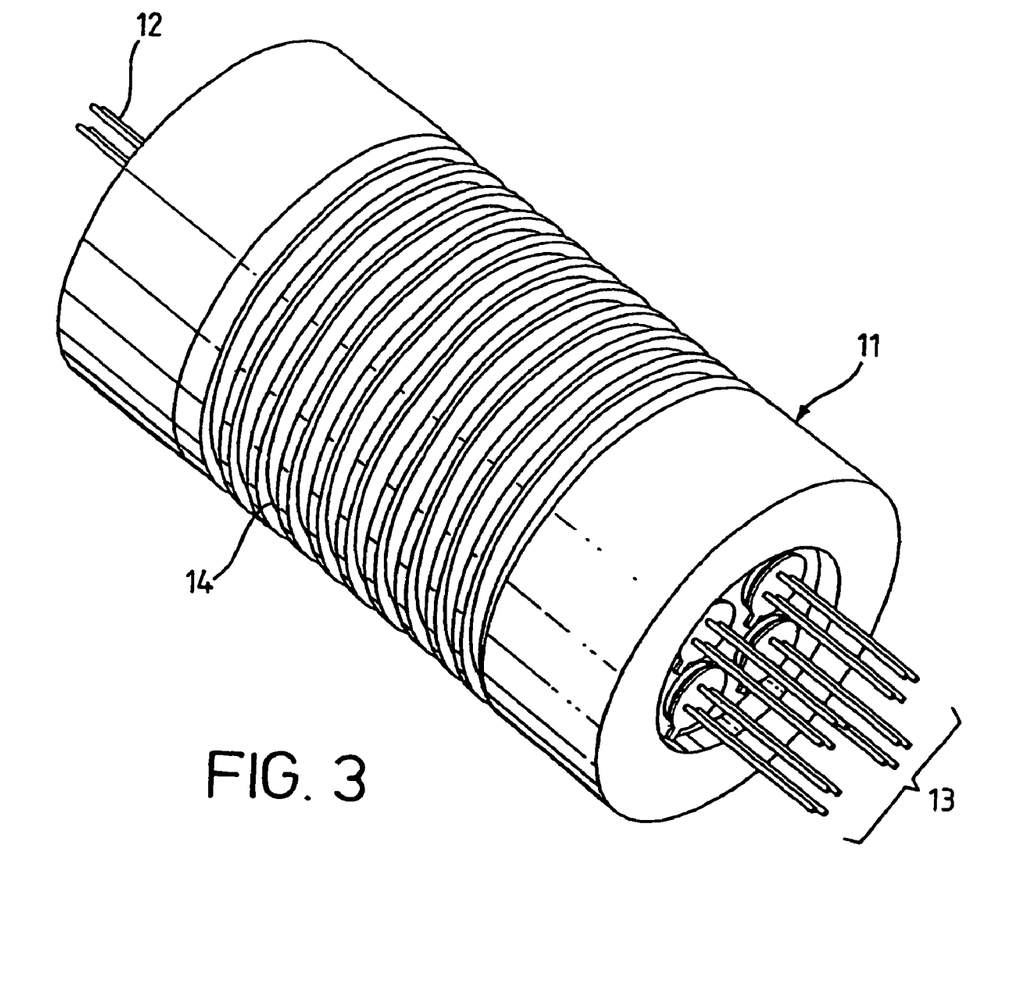
FIG. 3 is a perspective schematic view of the body of an alternative gas sensor constructed according to the invention.

An alternative body for a detector arrangement is shown in FIG. 3. In this embodiment, the body 11 comprises a cylinder. The source arrangement 12 is located at one end face of the cylinder 11 and a plurality 13 of detector arrangements is located at the other end face of the cylinder. The folded optical path comprises a helical groove 14 arranged around the outer surface of the cylinder 11. In use, radiation from the source arrangement 12 is directed along the folded optical path and is tapped off at various points to respective ones of the detector arrangements.

Figure 4:
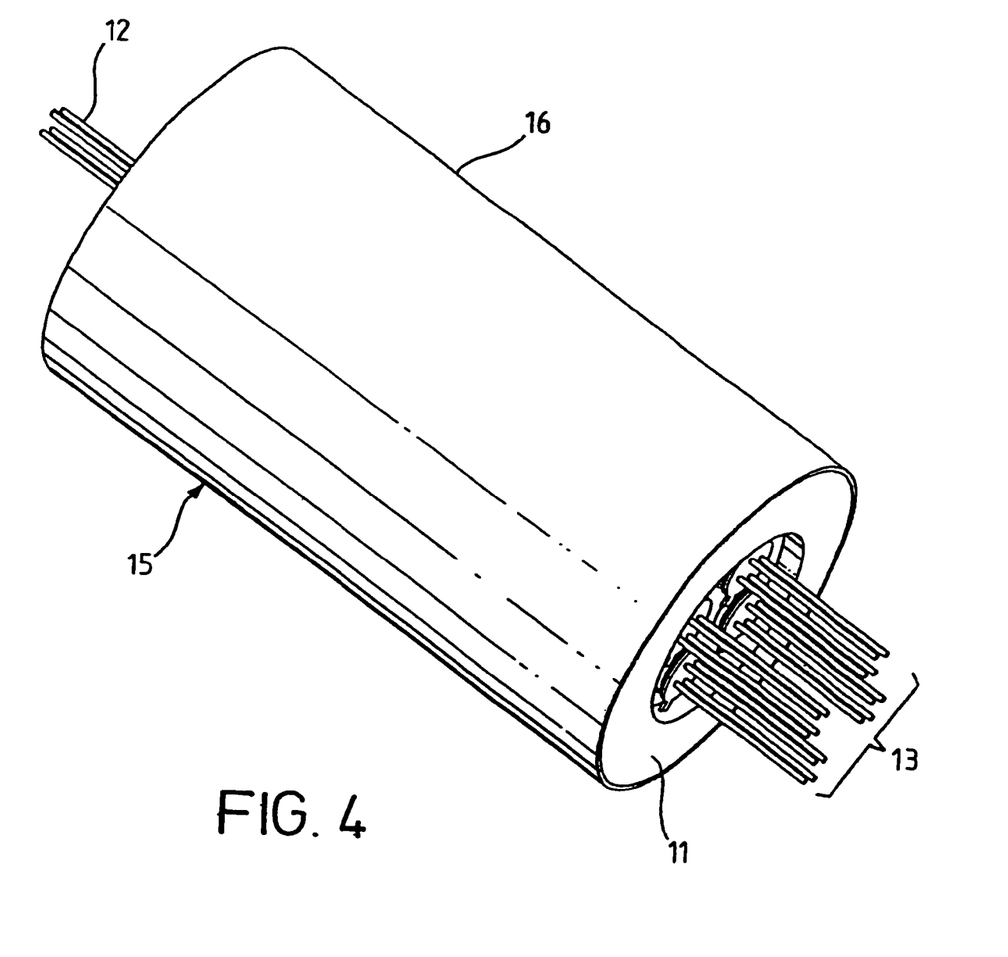
FIG. 4 is a perspective schematic view of a gas sensor incorporating the body of FIG. 3.

FIG. 4 illustrates a gas sensor 15 including the body 11 of FIG. 3. In this embodiment, a cylindrical sleeve 16 incorporating gas admittance means is provided and arranged to fit over the cylindrical body 11. The inner surface of the sleeve 16 is gold plated to provide good reflectance of radiation, in order to ensure that as much radiation as possible is directed along the optical path and is not absorbed within the device.

Figure 5:
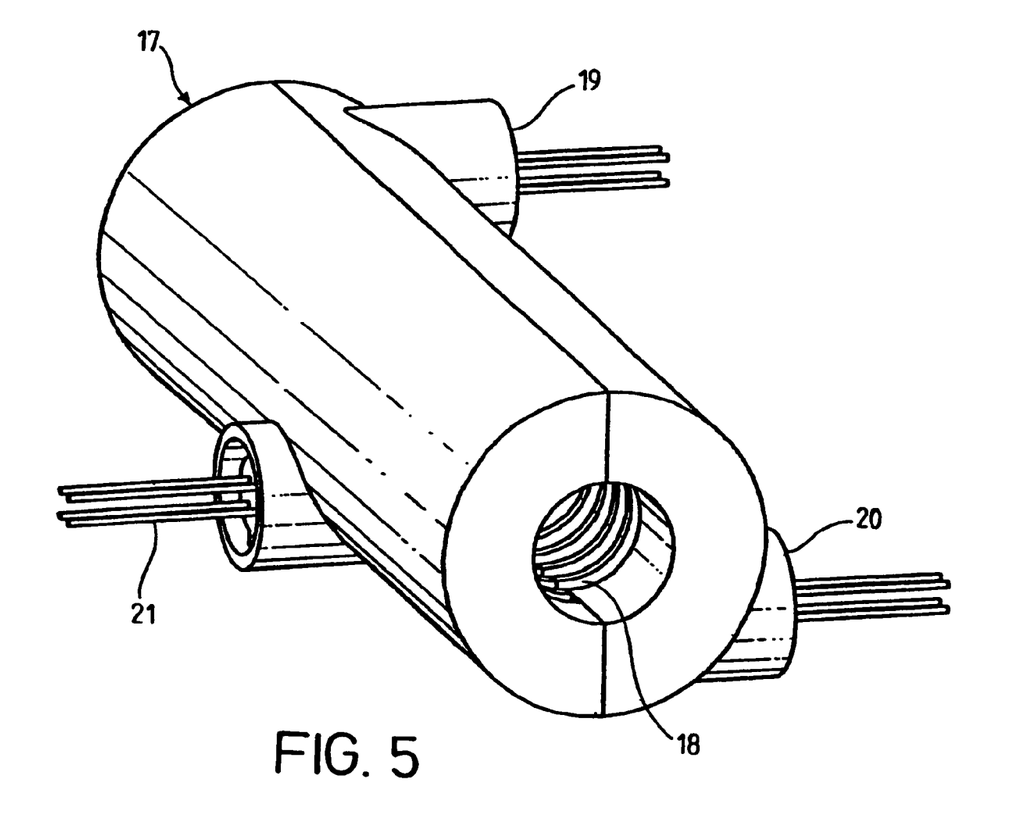
FIG. 5 is a perspective schematic view of another alternative gas sensor constructed according to the invention.

The gas sensor 17 of FIG. 5 also has a cylindrical body. However, in this embodiment, the cylinder is hollow along its longitudinal axis. The channel comprises a helical groove 18 arranged along the interior of the hollow cylinder 17. The source 19 is located at one end portion of the cylinder 17. A detector arrangement 20 is located at the other end portion of the cylinder 17. A further detector arrangement 21 is located partway along the cylinder 17. A cover for the channel formed by the groove may be provided, but is not shown in this drawing. The cover may comprise a cylindrical sleeve, arranged to fit inside the hollow. Gas may be directed into the hollow in order to ensure a sufficient sample for testing.

Figure 6:
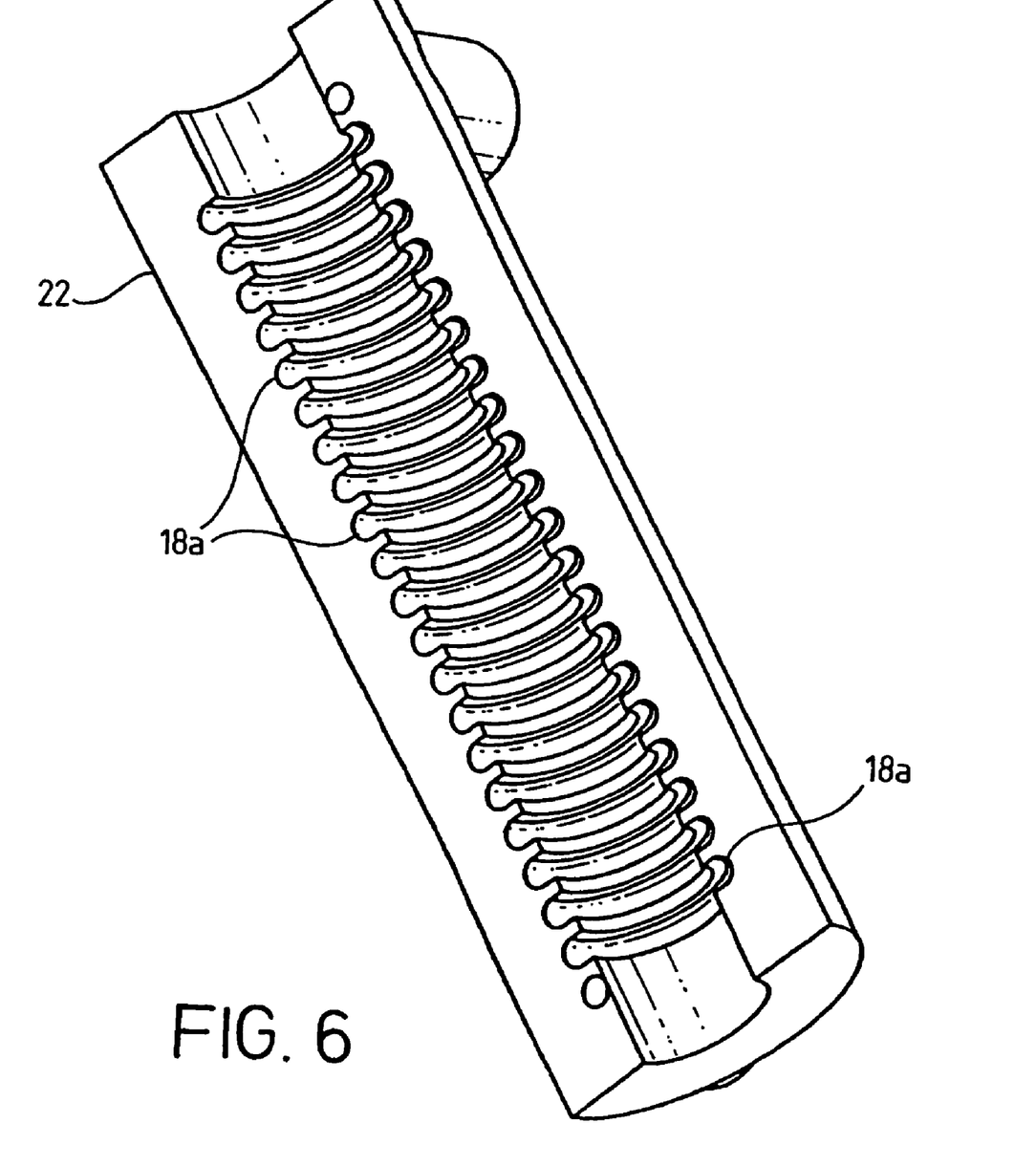
FIG. 6 is a perspective schematic view of a portion of the body of the sensor of FIG. 5.

The body of the sensor of FIG. 5 may be formed of two or more pieces, in order to simplify the manufacture of the folded optical path. A typical piece 22 is illustrated in FIG. 6. The piece 22 of the body is approximately u-shaped in section and comprises half of the hollow cylinder. A plurality of grooves 18a are formed along the hollow portion of the piece. These grooves are arranged to correspond with grooves on the other piece of the body such that, when the pieces are brought into registration, the plurality of grooves from the pieces form the helical optical path 18.

Figure 7:
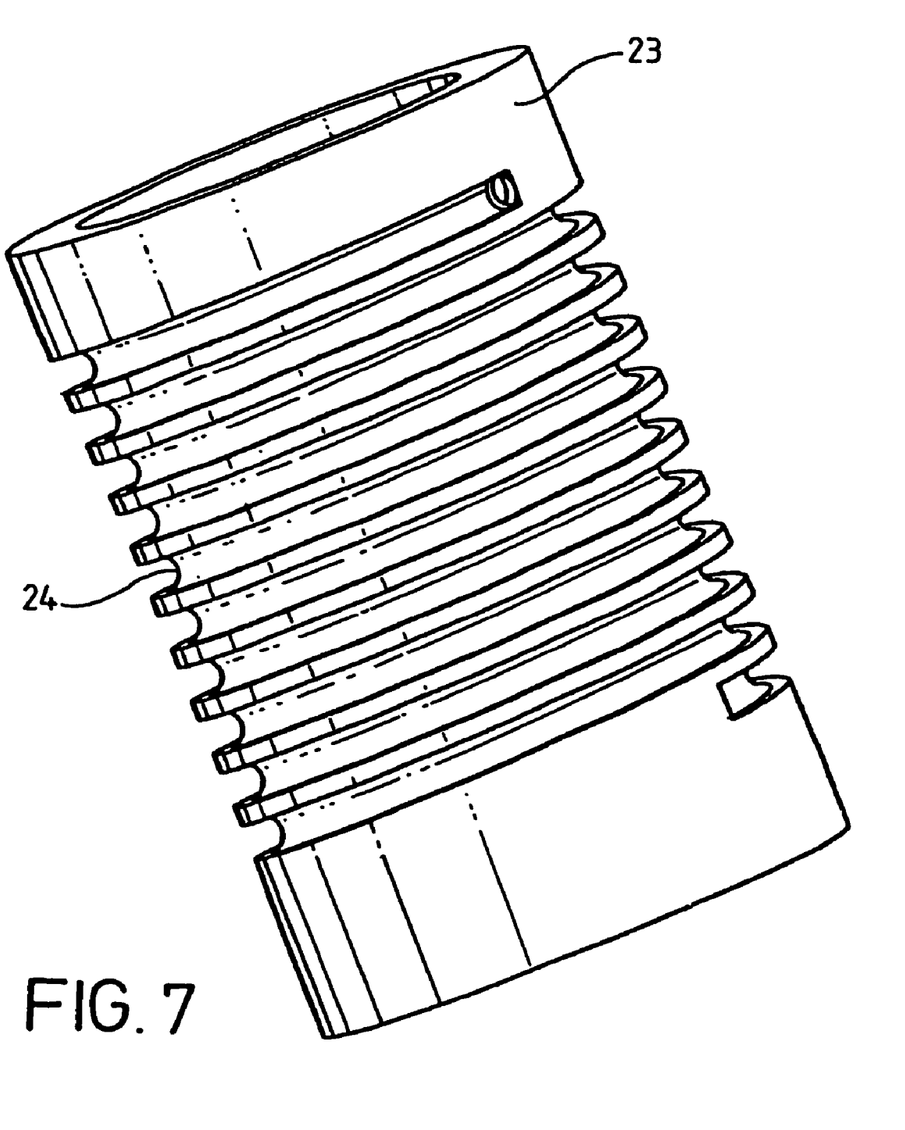
FIG. 7 is a perspective schematic view of an alternative or additional part of the body of the sensor of FIG. 5.

As an alternative to the gas sensor arrangements of FIGS. 4 and 5, radiation may be directed helically around both the interior and exterior of the sensor body. The sensor of FIG. 5 may thus be adapted by the inclusion of the body piece 23 as shown in FIG. 7. This body piece 23 comprises a hollow cylinder having a helical groove 24 on its exterior surface. Radiation from the source may be directed along the interior helical groove 18 followed by the exterior helical groove 24, or vice versa. A cylindrical sleeve may also be provided in this embodiment to cover the exterior helical groove 24 whilst providing gas admittance means.

Figure 8:
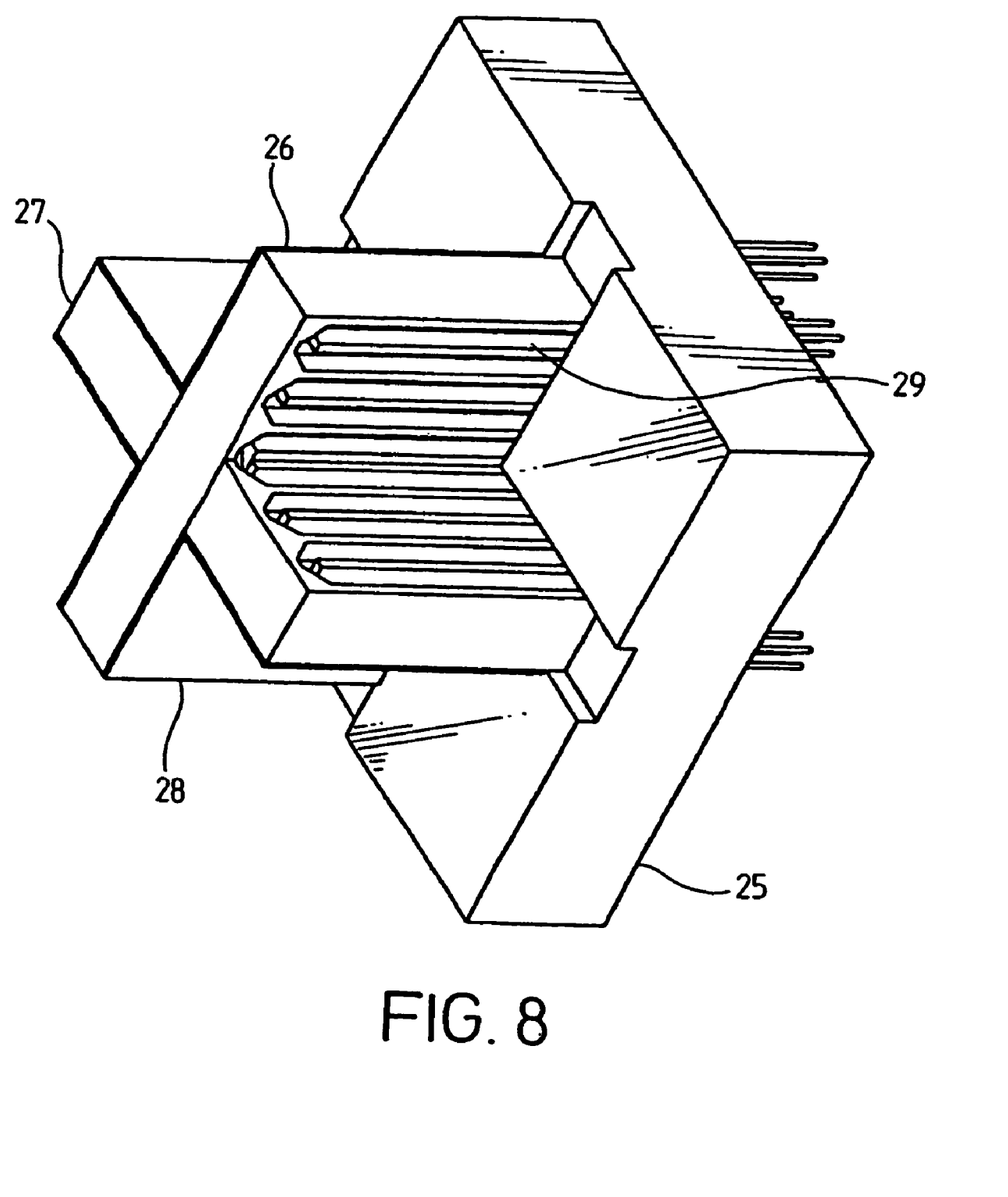
FIG. 8 is a perspective schematic view of the body of another alternative gas sensor constructed according to the invention.

In the alternative embodiment of FIG. 8, the body comprises a base portion 25 and walls 26, 27 extending from the base portion to form a cruciform portion 28 in plan view. The folded optical path comprises a serpentine groove 29 in the walls forming the cruciform portion 28. The parallel regions of the serpentine groove 29 extend transversely to the plane of the base 25. The curved portions of the serpentine groove 29 are located at the conjunction of the cruciform portion and the base, and also at the other end region of the cruciform walls remote from the base.

Figure 9:
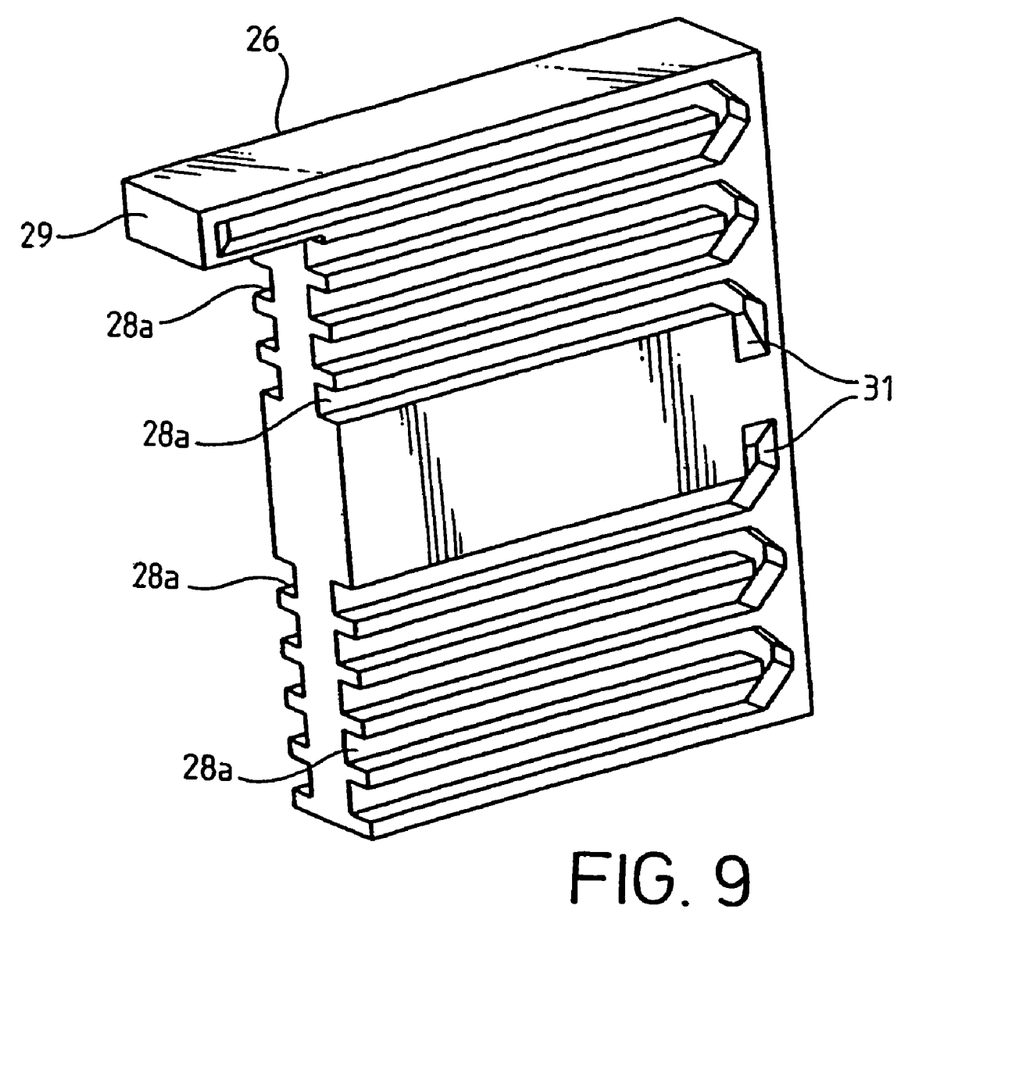
FIG. 9 is a perspective schematic view of a portion of the body of FIG. 8.

The cruciform portion 28 comprises two pieces 26, 27 arranged to substantially bisect each other transversely. One of the cruciform pieces 26 is shown in FIG. 9. The piece 26 includes portions of the serpentine groove 28a, which portions are arranged to correspond to serpentine groove portions in the other cruciform piece and with curved notches in the base in order to form a continuous serpentine groove along the surfaces of the walls of the cruciform portion. The piece 26 has an extended portion 29 that slots into a cavity in the base adjacent the source 30 of infrared radiation, as can be seen in FIG. 10.

Figure 10:
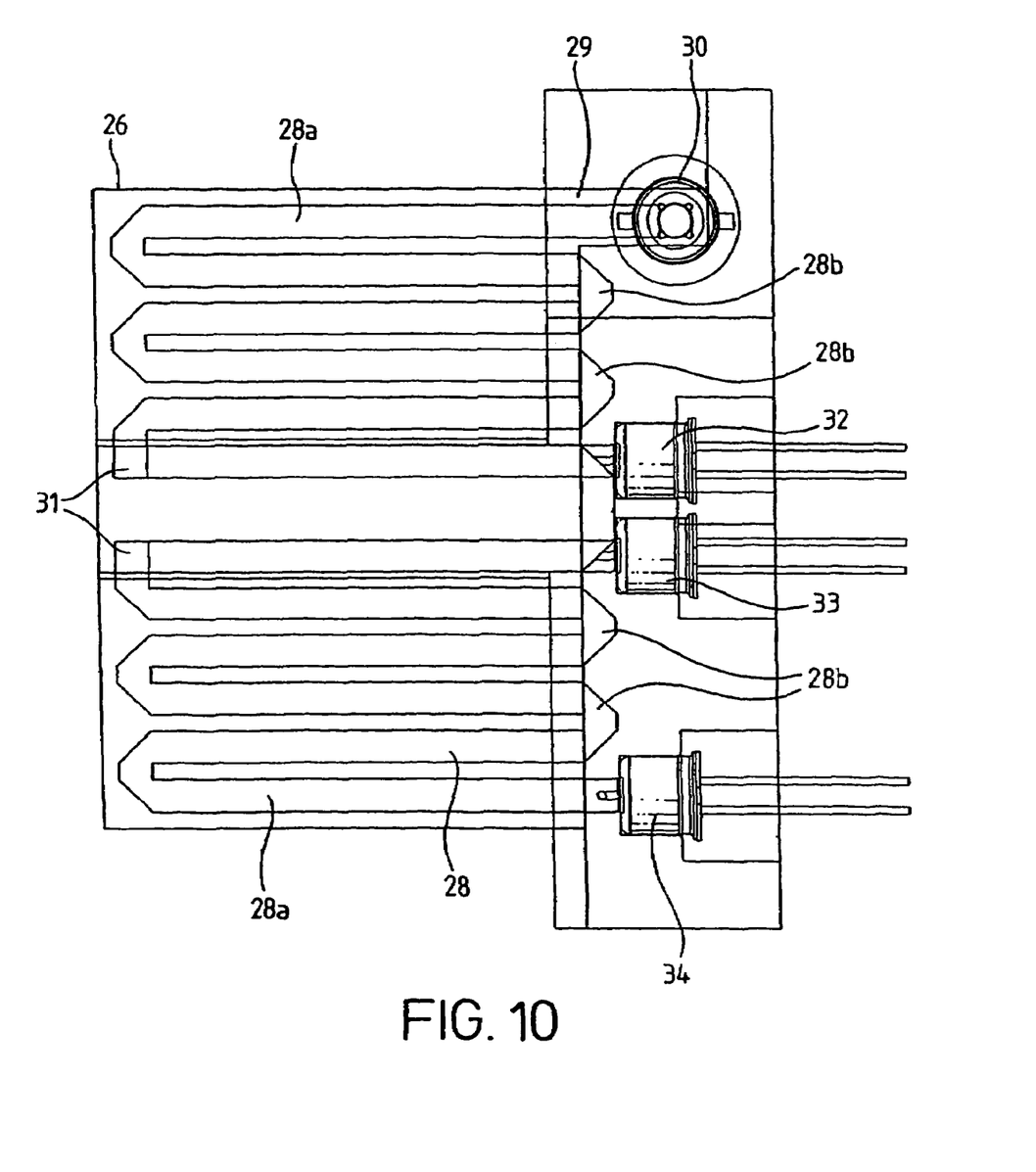

With reference to FIG. 10, this shows the piece of FIG. 9 slotted into the base portion 25. The face of the piece that was uppermost in FIG. 9 is directed into the page in FIG. 10. The extended portion 29 of the piece 26 slots into the base and is brought into registration with the source 30 of infrared radiation. Curved notches in the base 28b co-operate with the straight parallel serpentine groove portions 28a, resulting in a continuous serpentine groove 28 along the wall. Portions 31 of the grooves have reflective surfaces set at predetermined angles so as to direct radiation into and out of the transverse cruciform piece. The portions 31 are set at predetermined angles and are shown in detail in FIG. 9. The transverse cruciform portion also has a part-serpentine configuration that co-operates with further notches in the base to form the continuous serpentine optical path around the walls.

Detector arrangements 32, 33, 34 are located at predetermined positions adjacent the serpentine optical path. A portion of radiation is directed towards each detector arrangement at predetermined points along the channel.

Figure 11:
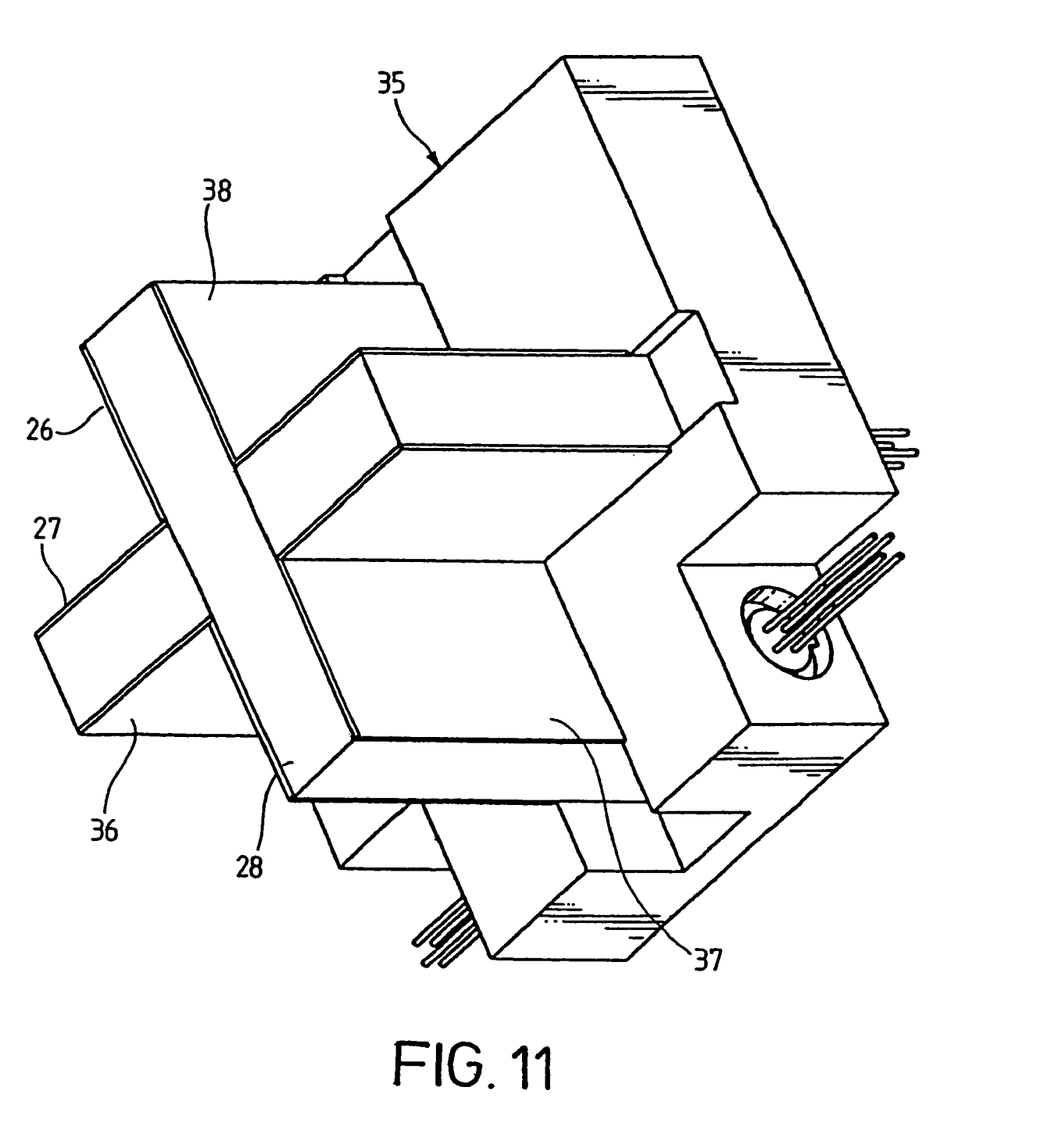
FIG. 11 is a perspective schematic view of a gas sensor incorporating the body of FIGS. 8 to 10.

FIG. 11 shows a gas sensor 35 employing the body of FIGS. 8 to 10. A plurality of flat panels, 36, 37, 38 etc., are provided to cover the walls 26, 27 of the cruciform portion 28. The inner surfaces of the panels are highly reflective and also include gas admittance means.

Figure 12:
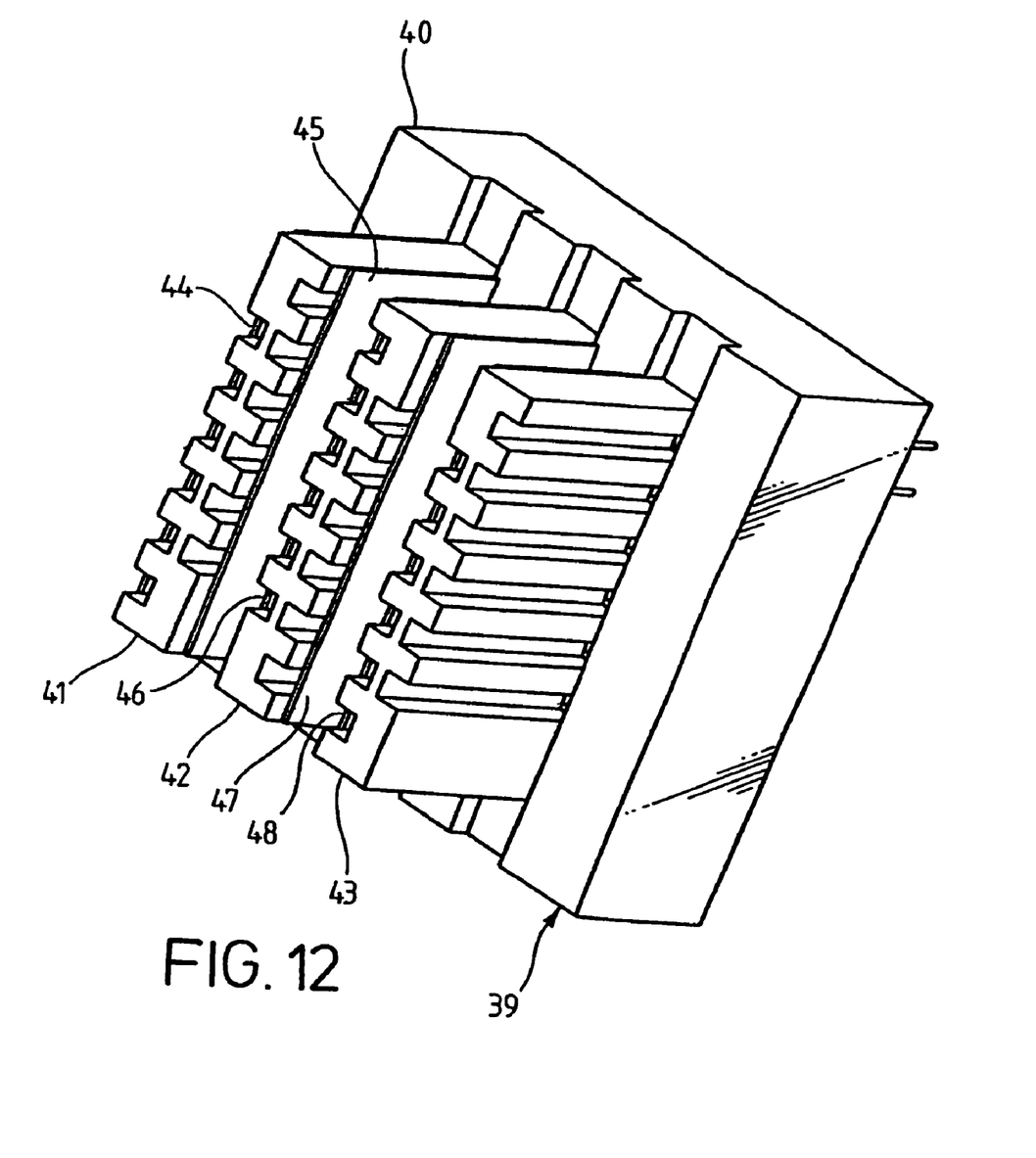
FIG. 12 is a perspective schematic view of part of the body of another alternative gas sensor constructed according to the invention.

A further alternative body 39 for a gas sensor is illustrated in FIG. 12. This sensor comprises a base portion 40 and a plurality of walls 41, 42, 43 extending from the base 40. Each wall 41, 42, 43 has a plurality of parallel grooves, arranged to be substantially perpendicular to the plane of the base portion. A plurality of panels 44 to 49 are provided, one for each side of the walls (panel 49 is omitted from FIG. 12 for clarity). These panels 44 to 49 have highly reflective interior surfaces and are also arranged to allow gas into the channels formed by the grooves.

Figure 13:
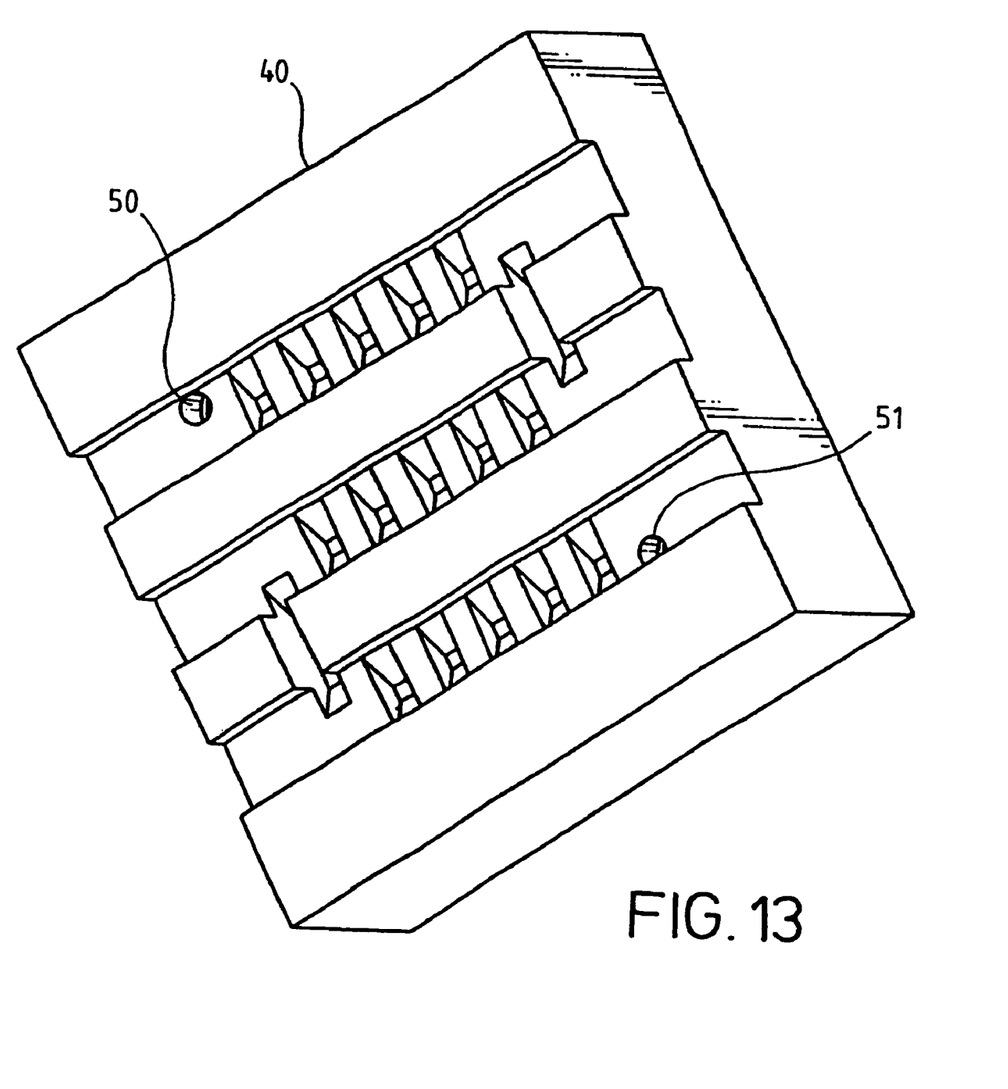
FIG. 13 is a perspective schematic view of a portion of the body of FIG. 12.

The base portion 40 is shown in more detail in FIG. 13. The base comprises apertures 50 and 51 arranged to accommodate a source of IR radiation and a detector. There are also a plurality of short notches in the base, arranged to reflect radiation emerging from a groove on one side of a wall into a corresponding groove on the other side of the same wall. The base also comprises a plurality of longer notches. These are arranged to reflect radiation from one wall to another. For example, radiation having reached the final groove on the first wall is directed into a groove at the end portion of the next wall.

Figure 14:
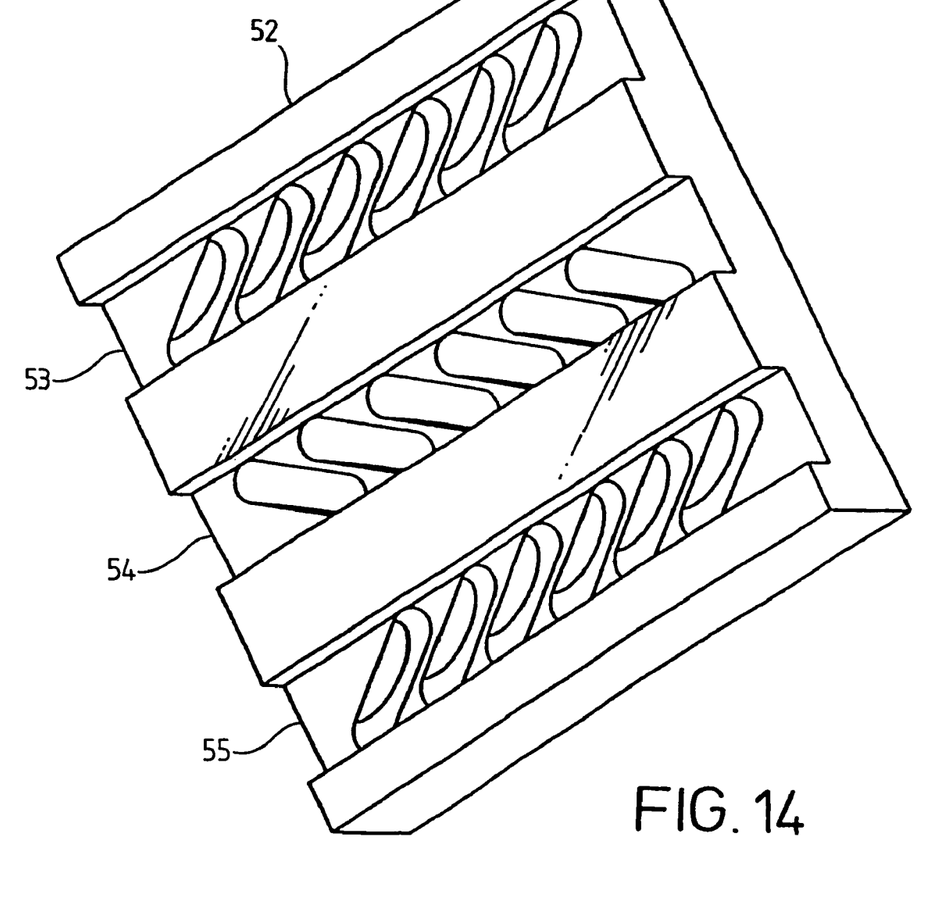
FIG. 14 is a perspective schematic view of another portion of the body of the sensor.

FIG. 14 illustrates a lid member 52 having slots 53, 54, 55 arranged to accommodate the end portions of the walls remote from the base portion. The slots in the lid member include short notches that are parallel to each other and extend diagonally from one side of the slot to the other. These notches are arranged to co-operate with the grooves in the walls to complete the folded optical path.

Figure 15:
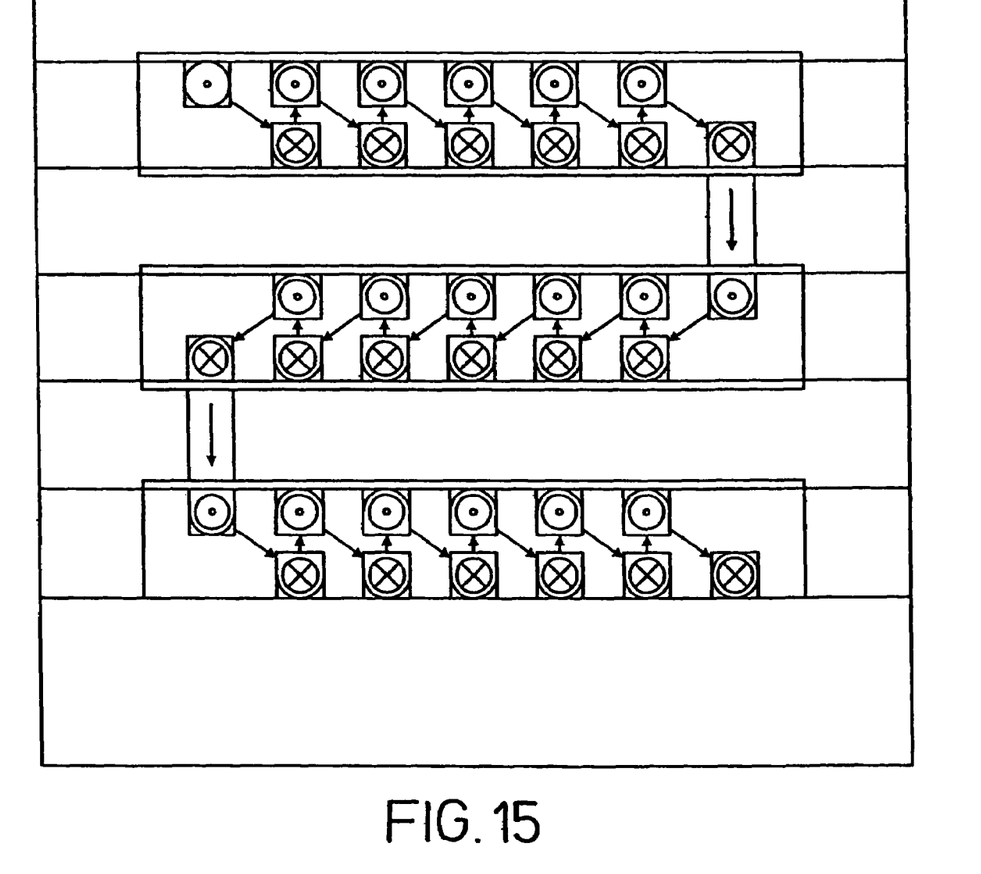
FIG. 15 is a sectional plan view of the body portion of FIG. 12, showing the path of radiation through the body of the sensor.

FIG. 15 is a schematic plan view of the body of FIG. 12. The lid portion has not been included in this drawing for clarity. This drawing shows the path of radiation along the grooves. The symbolic convention used here is the same as is used to designate the flow of electric current: the symbol of a cross in a circle designates radiation travelling into the page and the symbol of a dot in a circle designates radiation travelling out of the page. Thus, it can be seen that radiation being reflected along the channel takes an optical path that is approximately helical, with a rectangular cross section and resembling a sawtooth formation in plan view.

Figure 16:
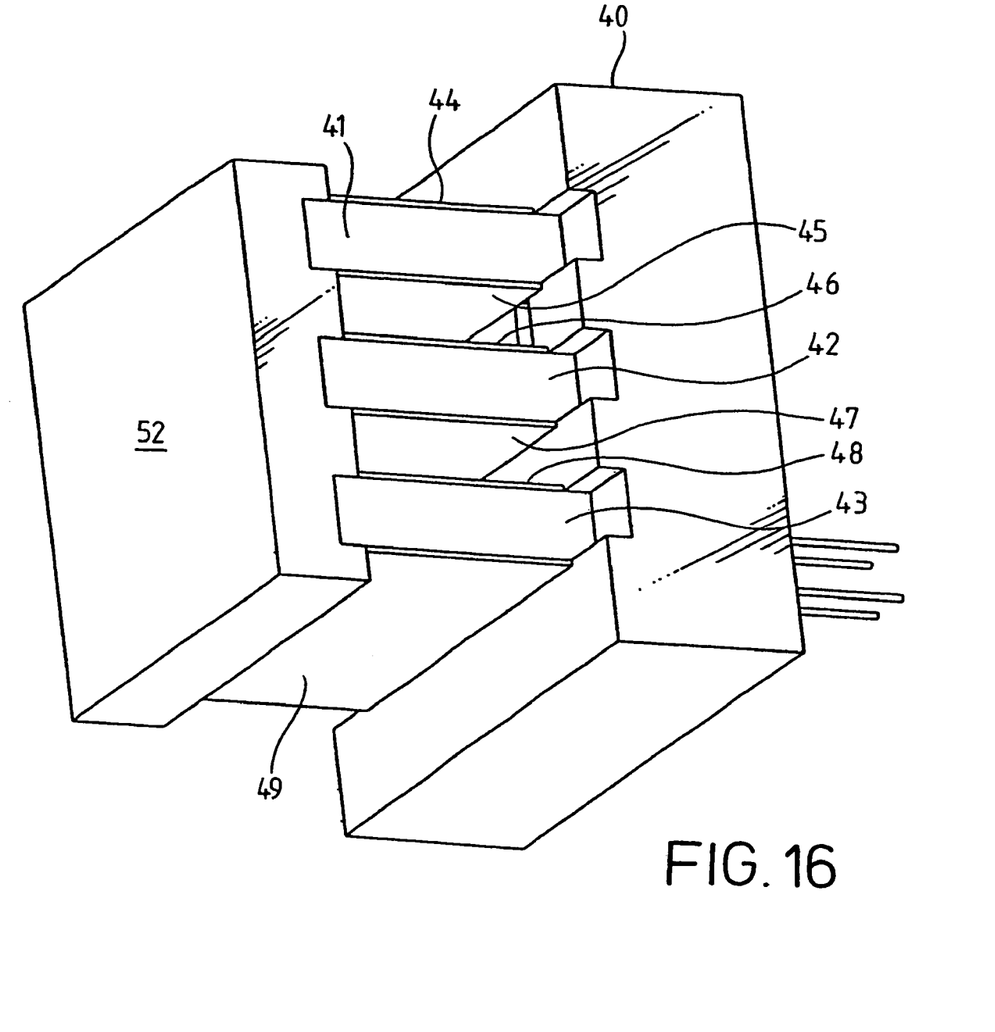
FIG. 16 is a perspective schematic view of a gas sensor incorporating the body portions of FIGS. 12 to 15.

FIG. 16 illustrates a gas sensor 56 incorporating all the body portions illustrated in FIGS. 12 to 15. The base portion 40, walls 41 to 43, panels 44 to 49 and lid member 52 are all visible.

The invention allows many configurations of optical path to be manufactured easily. The resulting sensor is mechanically stable and provides a long optical path within a confined space.

A suitable infrared source is an incandescent bulb, which provides a directional broadband infrared thermal source. Other sources include LEDs or lasers or diodes with immersion lenses.

Suitable detectors are photodiodes, thermopiles and pyroelectric detectors.

The body may be a single component or may comprise a plurality of pieces. A suitable manufacturing process for the contours of the chamber is that of machine turning. Alternatively, moulding in plastics or metal injection may be utilised. These processes are well known industrial techniques and may be readily employed by the skilled person.

The reflective surfaces may comprise layers of plated gold to provide good reflectance.

Channels having an approximately square cross-section have been illustrated, but rounded channel shapes may be employed, for example. Curved portions of the grooves may be formed by angular regions or rounded regions.

The invention claimed is:

1. A gas sensor comprising a body, the body comprising:
   a channel having a first end and a second end and arranged to admit a gas, the channel comprising an elongated groove having reflective surfaces defining a folded optical path for light from the source;
   an optical source located at the first end of the channel;
   a first detector, located at the second end of the channel, to detect light from the source; and
   a second detector located to detect light from the source that has been tapped off partway along the channel so that light detected by the second detector travels a shorter optical path than has light detected by the first detector.

2. A sensor as claimed in claim 1, wherein the second detector is connected to the channel by an optical pathway arranged to redirect a portion of light from a predetermined region of the channel to the second detector.

3. A sensor as claimed in claim 1, in which a portion of the elongated groove forms a spiral optical path.

4. A sensor as claimed in claim 1, in which a portion of the groove forms a serpentine optical path.

5. A sensor as claimed in claim 1, in which a portion of the groove forms a helical optical path.

6. A sensor as claimed in claim 5, in which the body is cylindrical and the helical optical path extends around the exterior of the body.

7. A sensor as claimed in claim 6, in which the cylinder includes a hollow region and a portion of the groove comprises a helical optical path around the interior of the hollow region.

8. A sensor as claimed in claim 5, in which the body includes a hollow cylindrical region and a portion of the groove comprises a helical optical path around the interior of the hollow region.

9. A sensor as claimed in claim 1, in which the body comprises a base arranged to accommodate the source and detector(s) and at least one wall extending transversely from the plane of the base.

10. A sensor as claimed in claim 9, in which the walls are arranged substantially to bisect each other transversely.

11. A sensor as claimed in claim 9, in which a portion of the elongated groove is located on the at least one wall and a portion of the groove is located on the base.

12. A sensor as claimed in claim 1, further comprising a cover for the channel including a gas admittance member.

13. A sensor as claimed in claim 12, in which the cover has an interior surface facing the channel, which surface is arranged to reflect radiation.

14. A sensor as claimed in claim 12, in which the gas admittance means includes sintered material.

15. A sensor as claimed in claim 12, in which the gas admittance means includes a particulate filter.

16. A sensor as claimed in claim 1 wherein the optical source is an infrared source.

* * * * *